(12) United States Patent
Saccomando et al.

(10) Patent No.: US 8,778,858 B2
(45) Date of Patent: Jul. 15, 2014

(54) AMINE DERIVATIVES AS FRICTION MODIFIERS IN LUBRICANTS

(75) Inventors: Daniel J. Saccomando, Sheffield (GB); Richard J. Vickerman, Stow, OH (US); Suzanne M. Patterson, Seven Hills, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 452 days.

(21) Appl. No.: 13/201,745

(22) PCT Filed: Feb. 11, 2010

(86) PCT No.: PCT/US2010/023867
§ 371 (c)(1), (2), (4) Date: Sep. 28, 2011

(87) PCT Pub. No.: WO2010/096325
PCT Pub. Date: Aug. 26, 2010

(65) Prior Publication Data
US 2012/0015855 A1    Jan. 19, 2012

Related U.S. Application Data

(60) Provisional application No. 61/153,396, filed on Feb. 18, 2009.

(51) Int. Cl.
*C07C 233/36* (2006.01)
*C10M 133/06* (2006.01)
*C10M 133/16* (2006.01)

(52) U.S. Cl.
USPC .......................................... 508/476; 508/562

(58) Field of Classification Search
USPC ................................. 508/476, 562
See application file for complete search history.

(56) References Cited

U.S. PATENT DOCUMENTS

| | | | |
|---|---|---|---|
| 3,028,402 A * | 4/1962 | Albrecht | 554/59 |
| 3,251,853 A | 5/1966 | Hoke | |
| 4,358,387 A * | 11/1982 | Zoleski et al. | 508/399 |
| 4,581,039 A | 4/1986 | Horodysky | |
| 4,789,493 A | 12/1988 | Horodysky | |
| 5,344,579 A | 9/1994 | Ohtani et al. | |
| 5,395,539 A | 3/1995 | Chandler et al. | |
| 5,441,656 A | 8/1995 | Ohtani et al. | |
| 5,916,852 A | 6/1999 | Nibert et al. | |
| 7,371,710 B2 * | 5/2008 | Morita | 508/156 |
| 7,521,403 B2 * | 4/2009 | Levine et al. | 508/554 |
| 2006/0058202 A1 | 3/2006 | Levine et al. | |
| 2006/0084583 A1 | 4/2006 | Tipton et al. | |
| 2008/0176777 A1 | 7/2008 | Milner et al. | |
| 2009/0005277 A1 | 1/2009 | Watts et al. | |
| 2010/0210490 A1 | 8/2010 | Vickerman et al. | |

FOREIGN PATENT DOCUMENTS

WO    2010/096321    8/2010

OTHER PUBLICATIONS

Corresponding PCT Publication and Search Report No. WO 2010/096325 A1 published Aug. 26, 2010.
Written Opinion from corresponding International Application No. PCT/US2010/023867 mailed Jul. 14, 2010.

* cited by examiner

*Primary Examiner* — Jim Goloboy
(74) *Attorney, Agent, or Firm* — David M. Shold, Esq.; Michael F. Esposito, Esq.

(57) ABSTRACT

A composition is provided for use as a friction modifier for an automatic transmission, comprising a long chain hydrocarbyl amine having one or two additional groups on one or two different amine nitrogen atom thereof of the structure —R3-C(=O)X(R4)c. R3 is an alkylene group or a group comprising a group of 1-4 carbon atoms or a chain of 2 to 9 carbon atoms interrupted by one or two nitrogen or oxygen atoms within the chain; X is nitrogen or oxygen, and R4 is a long chain hydrocarbyl group, or H, or —R3-NHR5. The compound does not contain a primary amino group.

20 Claims, No Drawings

AMINE DERIVATIVES AS FRICTION MODIFIERS IN LUBRICANTS

BACKGROUND OF THE INVENTION

The present invention relates to the field of additives for fluids such as automatic transmission fluids, manual transmission fluids, traction fluids, fluids for continuously variable transmission fluids (CVTs), dual clutch automatic transmission fluids, farm tractor fluids, gear oils, and engine lubricants.

In the automatic transmission marketplace, where there is rapid engineering change driven by the desire to reduce weight and increase transmission capacity, there is a desire for automatic transmission fluids that exhibit a high static coefficient of friction for improved clutch holding capacity. Continuously slipping torque converter clutches, for instance, impose exacting friction requirements on automatic transmission fluids (ATFs). The fluid must have a good friction versus sliding speed relationship, or an objectionable phenomenon called shudder will occur in the vehicle. Transmission shudder is a self-excited vibrational state commonly called "stick-slip" or "dynamic frictional vibration" generally occurring in slipping torque converter clutches. The friction characteristics of the fluid and material system, combined with the mechanical design and controls of the transmission, determine the susceptibility of the transmission to shudder. Plotting the measured coefficient of friction ($\mu$) versus sliding speed (V), commonly called a $\mu$-V curve, has been shown to correlate to transmission shudder. Both theory and experiments support the region of positive to slightly negative slope of this $\mu$-V curve to correlate to good anti-shudder performance of transmission fluids. A fluid which allows the vehicle to operate without vibration or shudder is said to have good "anti-shudder" performance. The fluid should maintain those characteristics over its service lifetime. The longevity of the anti-shudder performance in the vehicle is commonly referred to as "anti-shudder durability". The variable speed friction tester (VSFT) measures the coefficient of friction with respect to sliding speed simulating the speeds, loads, and friction materials found in transmission clutches and correlates to the performance found in actual use. The procedures are well documented in the literature; see for example Society of Automotive Engineers publication #941883.

The combined requirements of high static coefficient of friction and durable positive slope are often incompatible with traditional ATF friction modifier technology which is extremely well described in the patent literature. Many of the commonly used friction modifiers result in a low static coefficient of friction and are not durable enough on positive slope to be of sufficient use.

U.S. Pat. No. 5,395,539, Chandler et al., Mar. 7, 1995, discloses an amide containing friction modifier for use in power transmission fluids. The additive comprises a Component-1 formed by condensing a polyamine with an aliphatic monoacid.

U.S. Patent Application 2006/0058202, Levine et al., published Mar. 16, 2006, discloses certain amine derivatives of N-alkyl-halo-acetamides, which may be of the formula

where R, each independently, is alkyl or alkenyl of 1 to 8 carbon atoms.

U.S. Pat. No. 4,789,493, Horodysky, Dec. 6, 1988, discloses lubricants containing N-alkylalkylenediamine amides. Disclosed is $R^2$—$N(R^3)$—$R^1$—NH—$R^3$ wherein $R^1$ is a $C_2$ to $C_4$ alkylene group, $R^2$ must be a $C_{12}$ to $C_{30}$ hydrocarbyl group, and $R^3$ is H, a $C_1$-$C_3$ aliphatic group, or $R^4$—C(=O)—; at least one of the $R^3$s must be $R^4$—C(=O)—. $R^4$ is H or $C_{1-4}$. An example is Coco-NH—(CH$_2$)$_3$—NH—C(=O)H.

U.S. Pat. No. 4,581,039, Horodysky, Apr. 8, 1986 discloses lubricants containing N-hydrocarbyl hydrocarbylenediamine carboxylates, for example, the reaction product of N-oleyl-1, 3-propylenediamine with oleic acid. These are reported to have the formula

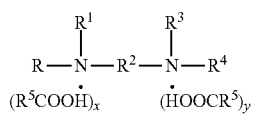

U.S. Pat. No. 5,344,579, Ohtani et al., Sep. 6, 1994, discloses a friction modifier system comprising a hydroxyalkyl aliphatic imidazoline, having on the 1-position on the ring a hydroxyalkyl group that contains from 2 to about 4 carbon atoms, and having in the adjacent 2-position on the ring a non-cyclic hydrocarbyl group containing about 10 to about 25 carbon atoms. A suitable compound is 1-hydroxyethyl-2-heptadecenyl imidazoline. Another component is a di(hydroxyalkyl) aliphatic tertiary amine. The hydrocarbyl group contains about 10 to about 25 carbon atoms. The hydroxyalkyl groups may be 2-hydroxyethyl groups.

U.S. Pat. No. 5,441,656, Ohtani et al., Aug. 15, 1995, discloses a friction modifier system that consists essentially of (i) an N-aliphatic hydrocarbyl-substituted diethanolamine and (ii) an N-aliphatic hydrocarbyl substituted trimethylenediamine.

U.S. Pat. No. 3,251,853, Hoke, May 17, 1966, discloses an oil-soluble acylated amine. In examples, reactants can xylyl-stearic acid or heptylphenyl-heptanoic acid, with tetraethylene pentamine or dodecylamine or N-2-aminoethyleoctadecylamine. An example is the condensation product of N-2-aminoethyl)octadecylamine with xylyl-stearic acid.

U.S. Pat. No. 5,916,852, Nibert et al. Jun. 29, 1999, discloses a power transmission fluid composition comprising, among others, an amine (i.e., alkyl primary amine) having the structure R—NH$_2$ where R is about a C8 to C30 alkyl. It may also include an amine containing friction modifier. The amine may be, among others, tallow amine. The amine containing friction modifier may be the reaction products of a long chain carboxylic acid (such as, e.g., stearic acid) with a polyamine, and may be of the structure

or may be an alkoxylated amine such as those produced by reacting a long chain primary amine with a low molecular weight alkoxide such as ethylene oxide or propylene oxide.

U.S. Patent publication 2009/0005277, Watts et al., Jan. 1, 2009, discloses lubricating oil compositions said to have excellent friction stability, comprising, among other components, a polyalkylene polyamine-based friction modifier that has been reacted with an acylating agent to convert at least one secondary amine group into an amide.

The disclosed technology, therefore, provides a friction modifier suitable for providing an automatic transmission fluid with a high coefficient of friction or a durable positive slope in a μ-V curve or both.

SUMMARY OF THE INVENTION

The disclosed technology provides a composition, which may be suitable for use as a friction modifier for an automatic transmission, comprising an oil of lubricating viscosity and a hydrocarbyl amine (which may optionally have more than one amine nitrogen atom, i.e., one or more), the hydrocarbyl group thereof having 12 to 22 carbon atoms, said amine having one or two groups in addition to said hydrocarbyl group, on one or more amine nitrogen atoms thereof, such additional group or groups independently being of the structure —$R^3$—C(=O)X($R^4$)$_c$, wherein each $R^3$ is independently an alkylene group containing 1 to 4 carbon atoms or a group containing a chain of 2 to 9 carbon atoms interrupted by one or two nitrogen or oxygen atoms within the chain; X is nitrogen or oxygen; c is 2 when X is nitrogen and 1 when X is oxygen; and each $R^4$ is independently a hydrocarbyl group of 1 to about 20 carbon atoms or a group represented by the formula —$R^3$—NH$R^5$ wherein $R^5$ is a hydrocarbyl group of about 12 to about 22 carbon atoms, or, if X is nitrogen, $R^4$ may be H. In certain embodiments the hydrocarbyl amine does not contain a primary amino group. (It may or may not contain a primary amino group independently of the presence or absence of any other groups on the molecule and independently of the presence or absence of any other materials present in the composition.)

The disclosed technology also provides a composition, which may be suitable for use as a friction modifier for an automatic transmission, comprising an oil of lubricating viscosity and a product obtained or obtainable by a process of reacting an N-(carboalkoxyalkyl)hydrocarbylamine (which may also be referred to as an N-hydrocarbylaminoester), the hydrocarbyl group thereof having 12 to 22 carbon atoms, with an N-hydrocarbyl substituted diamine, the hydrocarbyl group of the substituted diamine containing 12 to 22 carbon atoms. (In one embodiment the N-hydrocarbylaminoester may be a diester, i.e, an N-hydrocarbylaminodiester, i.e., an N,N-bis [carboxyalkyl])hydrocarbylamine.)

The disclosed technology also provides a lubricating composition comprising the herein-described friction modifiers in an oil of lubricating viscosity; and a method for lubricating an automatic transmission, comprising supplying thereto the lubricant as described herein.

DETAILED DESCRIPTION OF THE INVENTION

Various features and embodiments will be described below by way of non-limiting illustration.

One component which is used in the disclosed technology is an oil of lubricating viscosity, which can be present in a major amount, for a lubricant composition, or in a concentrate forming amount, for a concentrate. Suitable oils include natural and synthetic lubricating oils and mixtures thereof. In a fully formulated lubricant, the oil of lubricating viscosity is generally present in a major amount (i.e. an amount greater than 50 percent by weight). Typically, the oil of lubricating viscosity is present in an amount of 75 to 95 percent by weight, and often greater than 80 percent by weight of the composition.

Natural oils useful in making the inventive lubricants and functional fluids include animal oils and vegetable oils as well as mineral lubricating oils such as liquid petroleum oils and solvent-treated or acid-treated mineral lubricating oils of the paraffinic, naphthenic or mixed paraffinic/-naphthenic types which may be further refined by hydrocracking and hydrofinishing processes.

Synthetic lubricating oils include hydrocarbon oils and halo-substituted hydrocarbon oils such as polymerized and interpolymerized olefins, also known as polyalphaolefins; polyphenyls; alkylated diphenyl ethers; alkyl- or dialkylbenzenes; and alkylated diphenyl sulfides; and the derivatives, analogs and homologues thereof. Also included are alkylene oxide polymers and inter-polymers and derivatives thereof, in which the terminal hydroxyl groups may have been modified by esterification or etherification. Also included are esters of dicarboxylic acids with a variety of alcohols, or esters made from C5 to C12 monocarboxylic acids and polyols or polyol ethers. Other synthetic oils include silicon-based oils, liquid esters of phosphorus-containing acids, and polymeric tetrahydrofurans.

Unrefined, refined and rerefined oils, either natural or synthetic, can be used in the lubricants of the present invention. Unrefined oils are those obtained directly from a natural or synthetic source without further purification treatment. Refined oils have been further treated in one or more purification steps to improve one or more properties. They can, for example, be hydrogenated, resulting in oils of improved stability against oxidation.

In one embodiment, the oil of lubricating viscosity is an API Group I, Group II, Group III, Group IV, or Group V oil, including a synthetic oil, or mixtures thereof. In another embodiment, the oil is Groups II, III, IV, or V. These are classifications established by the API Base Oil Interchangeability Guidelines. Group III oils contain <0.03 percent sulfur and >90 percent saturates and have a viscosity index of >120. Group II oils have a viscosity index of 80 to 120 and contain <0.03 percent sulfur and >90 percent saturates. Polyalphaolefins are categorized as Group IV. The oil can also be an oil derived from hydroisomerization of wax such as slack wax or a Fischer-Tropsch synthesized wax. Such "Gas-to-Liquid" oils are typically characterized as Group III. Group V is encompasses "all others" (except for Group I, which contains >0.03% S and/or <90% saturates and has a viscosity index of 80 to 120).

In one embodiment, at least 50% by weight of the oil of lubricating viscosity is a polyalphaolefin (PAO). Typically, the polyalphaolefins are derived from monomers having from 4 to 30, or from 4 to 20, or from 6 to 16 carbon atoms. Examples of useful PAOs include those derived from 1-decene. These PAOs may have a viscosity of 1.5 to 150 mm$^2$/s (cSt) at 100° C. PAOs are typically hydrogenated materials.

The oils of the present technology can encompass oils of a single viscosity range or a mixture of high viscosity and low viscosity range oils. In one embodiment, the oil exhibits a 100° C. kinematic viscosity of 1 or 2 to 8 or 10 mm$^2$/sec (cSt). The overall lubricant composition may be formulated using oil and other components such that the viscosity at 100° C. is 1 or 1.5 to 10 or 15 or 20 mm$^2$/sec and the Brookfield viscosity (ASTM-D-2983) at −40° C. is less than 20 or 15 Pa-s (20,000 cP or 15,000 cP), such as less than 10 Pa-s, even 5 or less.

The present technology provides, as one component, an amine-containing compound that may be useful as a friction modifier, particularly for lubricating transmissions such as automatic transmissions. The amine may be selected from the category of amines which may be generally described as substituted hydrocarbyl amines. The hydrocarbyl group of the amine, that is, a hydrocarbyl group attached to the amino nitrogen, or attached to an amino nitrogen, may be described as a long chain hydrocarbyl group, by which is meant generally a hydrocarbyl group containing 12 to 22 carbon atoms. In other embodiments, the hydrocarbyl group may contain 12 to 20, 12 to 18, 12 to 16, 12 to 14, 14 to 20, 14 to 18, or 14 to 16 carbon atoms. The hydrocarbyl group may comprise a mixture of individual groups on different molecules having a variety of carbon numbers falling generally within the range of 12 to 20 carbon atoms, although molecules with hydrocarbyl groups falling outside this range may also be present. If a mixture of hydrocarbyl groups is present, they may be primarily of even carbon number (e.g., 12, 14, 16, 18, 20, 22) as is characteristic of groups derived from many naturally-occurring materials, or they may be a mixture of even and odd carbon numbers or, alternatively, an odd carbon number or a mixture of odd numbers. They may be branched, linear, or cyclic and may be saturated or unsaturated, or combinations thereof. In certain embodiments the hydrocarbyl groups may contain 16 to 18 carbon atoms, and sometimes predominantly 16 or predominantly 18. Specific examples include mixed "coco" groups, that is, cocoalkyl groups, from cocoamine (predominantly C12 and C14 amines) and mixed "tallow" groups, that is tallowalkyl groups, from tallowamine (predominantly C16 and C18 groups), stearyl, and isostearyl groups. The tallowalkyl groups may be hydrogenated or not hydrogenated.

In addition to the long chain hydrocarbyl group, the amine will have at least one additional group (other than hydrogen) on a nitrogen atom, and in certain embodiments on the same nitrogen atom bearing the long chain hydrocarbyl group. That is, the nitrogen atom of the amine (if there is but a single nitrogen atom under consideration) may contain one or two long chain hydrocarbyl groups as described above, may contain zero or 1 hydrogens, and may contain one or two additional groups as described below, such that the three valences of the nitrogen atom are satisfied.

The other group or groups on the amine nitrogen atom (or on one or more amine nitrogen atoms, if more than one is present in the molecule) will comprise a carboxy-containing group. If there are multiple such groups in the molecule, the groups may be the same or different from each other. The general structure of such a group will be

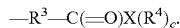

Here, $R^3$ will be a linking group which is attached to the amine nitrogen. If there are multiple $R^3$ groups, they may be the same or different from each other. They may be an alkylene group of 1 to 4 carbon atoms such as methylene, ethylene, ethylidene, propylene (in the 1,2 configuration, that is, methylethylene, or in the 1,3 configuration, that is, trimethylene), or butylene (in the 1,2 configuration or any other configurations such as 1,4, that is, tetramethylene). They may also comprise a chain of 2 to 8 or 2 to 9 carbon atoms interrupted by one or two nitrogen or oxygen atoms within the chain. Examples of these may include
—CH$_2$CH$_2$CH$_2$NHCH$_2$CH$_2$— or
—CH$_2$CH$_2$CH$_2$NHCH$_2$CH$_2$CH$_2$NHCH$_2$CH$_2$— or
—CH$_2$CH$_2$CH$_2$OCH$_2$CH$_2$— or —CH$_2$CH$_2$OCH$_2$CH$_2$— or
—CH$_2$CH$_2$CH$_2$NHCH$_2$—.

In the above structure, X may represent either oxygen or nitrogen. In the case of oxygen, the resulting group will be a carboxylic acid or an ester. In the case of nitrogen, the resulting group will be an amide. One or two $R^4$ groups will be attached to the X to satisfy its valence: one such group for oxygen and two such groups for nitrogen. That is, c will be 1 or 2, as the case may be. If a mixture of materials is present such that some of the Xs are nitrogen and some are oxygen, then c may have a fractional value between 1 and 2, but it will be either 1 or 2 for any given molecule. The $R^4$ group or groups may independently be hydrogen, or a hydrocarbyl group of 1 to 20 carbon atoms, such as 12 to 20 carbon atoms (as described above) or a nitrogen-containing group represented by the formula

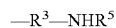

where $R^3$ is as defined above and $R^5$ is a hydrocarbyl group of 12 to 20 carbon atoms, as described above. (The $R^3$ contained within the $R^4$ group need not be identical to any of the $R^3$ linking groups as used above, as is implicit from the statement that each $R^3$ is independently one of the groups listed.) Specific examples of —C(=O)X($R^4$)$_c$ groups include —COOH, —CONH$_2$, —COOCH$_3$, —CONHCH$_3$, —CON(CH$_3$)$_2$, —CONH-coco, —CONH-tallow, and —CONH—CH$_2$CH$_2$NH-tallow, where "coco" and "tallow" are the hydrocarbyl residues of cocoamine and tallowamine, as described above.

Certain of these amines may also be represented by the formula

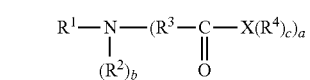

In this formula, $R^1$ is a hydrocarbyl group of 12 to 20 or 12 to 18 or 16 to 18 carbon atoms, or $R^1$ is an aminoalkyl group of up to 3 carbon atoms substituted on the nitrogen atom thereof by a hydrocarbyl group of 12 to 22 carbon atoms; $R^2$ is hydrogen or a hydrocarbyl group; a is 1 or 2, and b is 2−a. That is, there may be 1 or 2 —R$^3$—C(=O)X(R$^4$)$_c$ groups on the amine nitrogen. If there are multiple amine nitrogen atoms in the molecule and if there are multiple —R$^3$—C(=O)X(R$^4$)$_c$ groups, such groups may be attached to the same or to different nitrogens.

Some specific examples of the amines of the disclosed technology include those represented by the following structures:

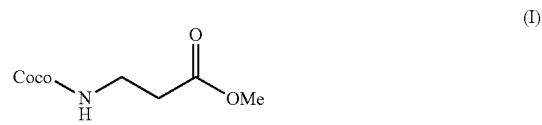
(I)

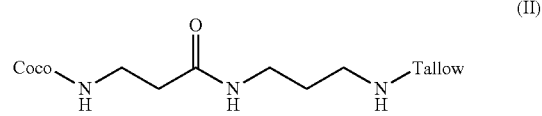
(II)

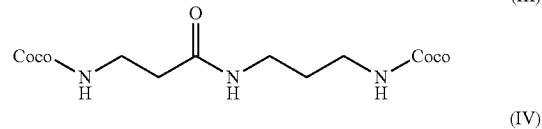
(III)

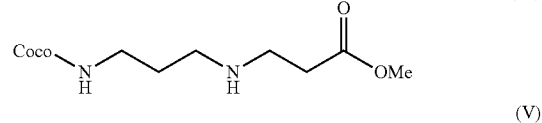
(IV)

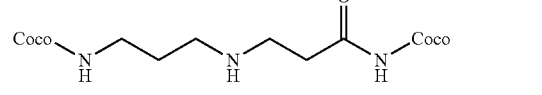
(V)

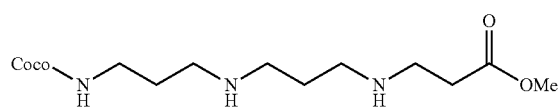
(VI)

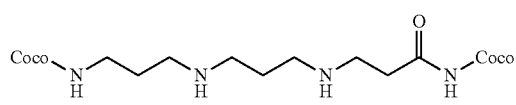
(VII)

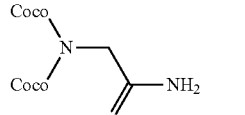
(VIII)

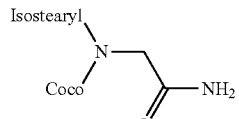
(IX)

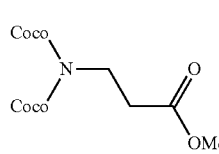
(X)

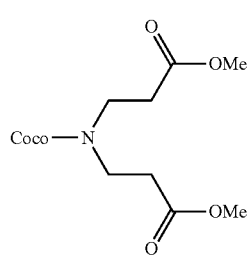
(XI)

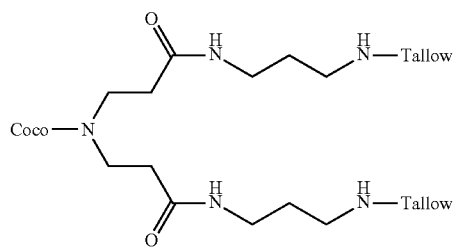
(XII)

or more generally

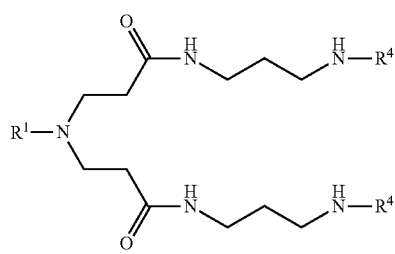
(XIIa)

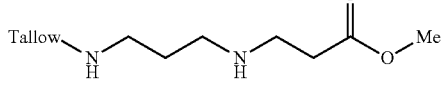
(XIII)

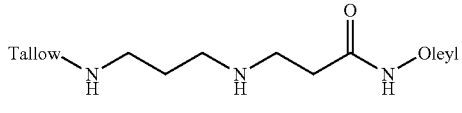
(XIV)

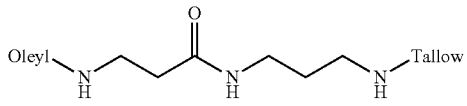
(XV)

where Me represents a methyl group and coco, tallow, $R^1$ and $R^4$ are as defined above. In certain embodiments, $R^1$ is a hydrocarbyl group of 12 to 22 carbon atoms and each $R^4$ is independently a hydrocarbyl group of 1 to 20 carbon atoms, or H, or a group represented by the formula —$R^3$—$NHR^5$ wherein $R^5$ is a hydrocarbyl group of 12 to 22 carbon atoms.

Certain of the amines of the present invention (that is, containing the carbonyl functionality) may be obtained by reaction of an amine with an equivalent amount of an unsaturated ester such as methyl acrylate. A generalized reaction scheme would be as follows:

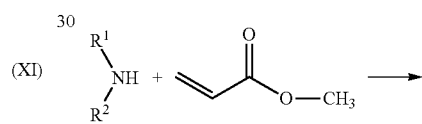

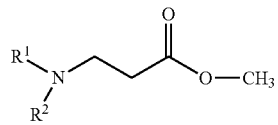

and the resulting ester may be converted to an amide or other functionality by known methods. The starting amine, designated here as $R^1R^2NH$ may have suitable R groups provided that at least one of them is selected so as to meet the requirements of the present invention, e.g., containing a hydrocarbyl group of 12 to 22 carbon atoms. In certain embodiments the precursor amine itself $R^1R^2NH$ may be a polyamine in the "Duomeen" series, available from Akzo, having a general structure such as

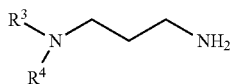

Such polyamines may be prepared by the addition of the monoamine $R^3R^4NH$ to acrylonitrile, by analogy to the above reaction to prepare the amino ester,

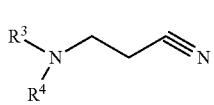

followed by catalytic reduction of the resulting nitrile compound, using, e.g., $H_2$ over Pd/C catalyst, to give the diamine.

In the event that the precursor amine is a diamine or a triamine, reaction of said amine with an unsaturated ester such as methyl acrylate may lead to addition of two molecules of the acrylate onto a single primary amino nitrogen. Alternatively, one molecule may add onto one nitrogen and a second may add onto a second nitrogen. Representative examples would thus also include the following:

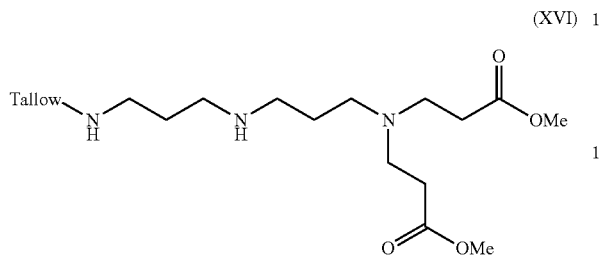

(XVI)

(in which two —$R^3$—C(=O)X($R^4$)$_c$ groups are on one amine nitrogen)

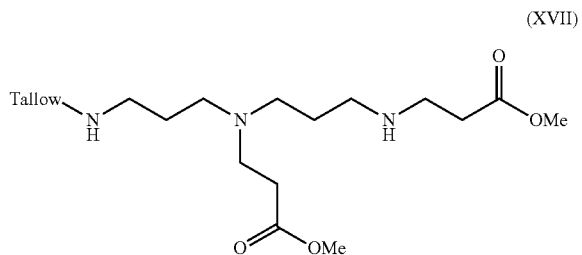

(XVII)

(in which the two groups are on two (i.e., multiple) amine nitrogen atoms). Both types of such materials and mixtures of such materials are contemplated and are to be considered to be a part of the reaction product of the corresponding precursors.

The amount of the amine in a fully formulated lubricant may be 0.1 to 10 percent by weight, or 0.5 to 6 percent or 0.8 to 4 percent, or 1 to 2.5 percent Other components may be present. One such component is a dispersant. It may be described as "other than an amine compound as described above" in the event that some of the amine compounds described above may exhibit some dispersant characteristics. Examples of "carboxylic dispersants" are described in many U.S. patents including the following: U.S. Pat. Nos. 3,219,666, 3,316,177, 3,340,281, 3,351,552, 3,381,022, 3,433,744, 3,444,170, 3,467,668, 3,501,405, 3,542,680, 3,576,743, 3,632,511, 4,234,435, Re 26,433, and 6,165,235.

Succinimide dispersants, a species of carboxylic dispersants, are prepared by the reaction of a hydrocarbyl-substituted succinic anhydride (or reactive equivalent thereof, such as an acid, acid halide, or ester) with an amine, as described above. The hydrocarbyl substituent group generally contains an average of at least 8, or 20, or 30, or 35 up to 350, or to 200, or to 100 carbon atoms. In one embodiment, the hydrocarbyl group is derived from a polyalkene. Such a polyalkene can be characterized by an $\overline{M}_n$ (number average molecular weight) of at least 500. Generally, the polyalkene is characterized by an $\overline{M}_n$ of 500, or 700, or 800, or 900 up to 5000, or to 2500, or to 2000, or to 1500. In another embodiment $\overline{M}_n$ varies from 500, or 700, or 800, to 1200 or 1300. In one embodiment the polydispersity ($\overline{M}_w/\overline{M}_n$) is at least 1.5.

The polyalkenes include homopolymers and inter-polymers of polymerizable olefin monomers of 2 to 16 or to 6, or to 4 carbon atoms. The olefins may be monoolefins such as ethylene, propylene, 1-butene, isobutene, and 1-octene; or a polyolefinic monomer, such as diolefinic monomer, such 1,3-butadiene and isoprene. In one embodiment, the inter-polymer is a homo-polymer. An example of a polymer is a polybutene. In one instance about 50% of the polybutene is derived from isobutylene. The polyalkenes can be prepared by conventional procedures.

In one embodiment, the succinic acylating agents are prepared by reacting a polyalkene with an excess of maleic anhydride to provide substituted succinic acylating agents wherein the number of succinic groups for each equivalent weight of substituent group is at least 1.3, e.g., 1.5, or 1.7, or 1.8. The maximum number of succinic groups per substituent group generally will not exceed 4.5, or 2.5, or 2.1, or 2.0. The preparation and use of substituted succinic acylating agents wherein the substituent is derived from such polyolefins are described in U.S. Pat. No. 4,234,435.

The substituted succinic acylating agent can be reacted with an amine, including those amines described above and heavy amine products known as amine still bottoms. The amount of amine reacted with the acylating agent is typically an amount to provide a mole ratio of CO:N of 1:2 to 1:0.25, or 1:2 to 1:0.75. If the amine is a primary amine, complete condensation to the imide can occur. Varying amounts of amide product, such as the amidic acid, may also be present. If the reaction is, rather, with an alcohol, the resulting dispersant will be an ester dispersant. If both amine and alcohol functionality are present, whether in separate molecules or in the same molecule (as in the above-described condensed amines), mixtures of amide, ester, and possibly imide functionality can be present. These are the so-called ester-amide dispersants.

"Amine dispersants" are reaction products of relatively high molecular weight aliphatic or alicyclic halides and amines, such as polyalkylene polyamines. Examples thereof are described in the following U.S. Pat. Nos. 3,275,554, 3,438,757, 3,454,555, and 3,565,804.

"Mannich dispersants" are the reaction products of alkyl phenols in which the alkyl group contains at least 30 carbon atoms with aldehydes (especially formaldehyde) and amines (especially polyalkylene polyamines). The materials described in the following U.S. patents are illustrative: U.S. Pat. Nos. 3,036,003, 3,236,770, 3,414,347, 3,448,047, 3,461,172, 3,539,633, 3,586,629, 3,591,598, 3,634,515, 3,725,480, 3,726,882, and 3,980,569.

Post-treated dispersants are also part of the present invention. They are generally obtained by reacting carboxylic, amine or Mannich dispersants with reagents such as urea, thiourea, carbon disulfide, aldehydes, ketones, carboxylic acids, hydrocarbon-substituted succinic anhydrides, nitriles, epoxides, boron compounds such as boric acid (to give "borated dispersants"), phosphorus compounds such as phosphorus acids or anhydrides, or 2,5-dimercaptothiadiazole (DMTD). Exemplary materials of this kind are described in the following U.S. Pat. Nos. 3,200,107, 3,282,955, 3,367,943, 3,513,093, 3,639,242, 3,649,659, 3,442,808, 3,455,832, 3,579,450, 3,600,372, 3,702,757, and 3,708,422.

Mixtures of dispersants can also be used. The amount of dispersant or dispersants, if present in formulations of the present technology, is generally 0.3 to 10 percent by weight. In other embodiments, the amount of dispersant is 0.5 to 7 percent or 1 to 5 percent of the final blended fluid formulation. In a concentrate, the amounts will be proportionately higher.

Another component frequently used is a viscosity modifier. Viscosity modifiers (VM) and dispersant viscosity modifiers (DVM) are well known. Examples of VMs and DVMs may include polymethacrylates, polyacrylates, polyolefins, styrene-maleic ester copolymers, and similar polymeric substances including homopolymers, copolymers and graft copolymers. The DVM may comprise a nitrogen-containing methacrylate polymer, for example, a polymer made using a nitrogen-containing methacrylate monomer derived from methyl methacrylate and dimethylaminopropyl amine.

Examples of commercially available VMs, DVMs and their chemical types may include the following: polyisobutylenes (such as Indopol™ from BP Amoco or Parapol™ from ExxonMobil); olefin copolymers (such as Lubrizol™ 7060, 7065, and 7067 from Lubrizol and Lucant™ HC-2000L and HC-600 from Mitsui); hydrogenated styrene-diene copolymers (such as Shellvis™ 40 and 50, from Shell and LZ® 7308, and 7318 from Lubrizol); styrene/maleate copolymers, which are dispersant copolymers (such as LZ® 3702 and 3715 from Lubrizol); polymethacrylates, some of which have dispersant properties (such as those in the Viscoplex™ series from RohMax, the Hitec™ series from Afton, and LZ 7702™, LZ 7727™, LZ 7725™ and LZ 7720C™ from Lubrizol); olefin-graft-polymethacrylate polymers (such as Viscoplex™ 2-500 and 2-600 from RohMax); and hydrogenated polyisoprene star polymers (such as Shellvis™ 200 and 260, from Shell). Also included are Asteric™ polymers from Lubrizol (methacrylate polymers with radial or star architecture). Viscosity modifiers that may be used are described in U.S. Pat. Nos. 5,157,088, 5,256,752 and 5,395,539. The VMs and/or DVMs may be used in the functional fluid at a concentration of up to 20% by weight. Concentrations of 1 to 12%, or 3 to 10% by weight may be used.

Another component that may be used in the composition used in the present technology is a supplemental friction modifier. These friction modifiers are well known to those skilled in the art. A list of friction modifiers that may be used is included in U.S. Pat. Nos. 4,792,410, 5,395,539, 5,484,543 and 6,660,695. U.S. Pat. No. 5,110,488 discloses metal salts of fatty acids and especially zinc salts, useful as friction modifiers. A list of supplemental friction modifiers that may be used may include:

| | |
|---|---|
| fatty phosphites | borated alkoxylated fatty amines |
| fatty acid amides | metal salts of fatty acids |
| fatty epoxides | sulfurized olefins |
| borated fatty epoxides | fatty imidazolines |
| fatty amines other than the fatty amines discussed above | condensation products of carboxylic acids and polyalkylene-polyamines |
| glycerol esters | metal salts of alkyl salicylates |
| borated glycerol esters | amine salts of alkylphosphoric acids |
| alkoxylated fatty amines | ethoxylated alcohols |
| oxazolines | imidazolines |
| hydroxyalkyl amides | polyhydroxy tertiary amines | and mixtures of two or more thereof.

Representatives of each of these types of friction modifiers are known and are commercially available. For instance, fatty phosphites may be generally of the formula $(RO)_2PHO$ or $(RO)(HO)PHO$ where R may be an alkyl or alkenyl group of sufficient length to impart oil solubility. Suitable phosphites are available commercially and may be synthesized as described in U.S. Pat. No. 4,752,416.

Borated fatty epoxides that may be used are disclosed in Canadian Patent No. 1,188,704. These oil-soluble boron-containing compositions may be prepared by reacting a boron source such as boric acid or boron trioxide with a fatty epoxide which may contain at least 8 carbon atoms. Non-borated fatty epoxides may also be useful as supplemental friction modifiers.

Borated amines that may be used are disclosed in U.S. Pat. No. 4,622,158. Borated amine friction modifiers (including borated alkoxylated fatty amines) may be prepared by the reaction of a boron compounds, as described above, with the corresponding amines, including simple fatty amines and hydroxy containing tertiary amines. The amines useful for preparing the borated amines may include commercial alkoxylated fatty amines known by the trademark "ETHOMEEN" and available from Akzo Nobel, such as bis[2-hydroxyethyl]-cocoamine, polyoxyethylene[10]cocoamine, bis[2-hydroxyethyl]-soyamine, bis[2-hydroxyethyl]-tallowamine, polyoxyethylene-[5]tallowamine, bis[2-hydroxyethyl]oleylamine, bis[2-hydroxyethyl]octadecylamine, and polyoxyethylene[15]octadecylamine. Such amines are described in U.S. Pat. No. 4,741,848.

Alkoxylated fatty amines and fatty amines themselves (such as oleylamine) may be useful as friction modifiers. These amines are commercially available.

Both borated and unborated fatty acid esters of glycerol may be used as friction modifiers. Borated fatty acid esters of glycerol may be prepared by borating a fatty acid ester of glycerol with a boron source such as boric acid. Fatty acid esters of glycerol themselves may be prepared by a variety of methods well known in the art. Many of these esters, such as glycerol monooleate and glycerol tallowate, are manufactured on a commercial scale. Commercial glycerol monooleates may contain a mixture of 45% to 55% by weight mono-ester and 55% to 45% by weight diester.

Fatty acids may be used in preparing the above glycerol esters; they may also be used in preparing their metal salts, amides, and imidazolines, any of which may also be used as friction modifiers. The fatty acids may contain 6 to 24 carbon atoms, or 8 to 18 carbon atoms. A useful acid may be oleic acid. The amides of fatty acids may be those prepared by condensation with ammonia or with primary or secondary amines such as diethylamine and diethanolamine. Fatty imidazolines may include the cyclic condensation product of an acid with a diamine or polyamine such as a polyethylenepolyamine. In one embodiment, the friction modifier may be the condensation product of a C8 to C24 fatty acid with a polyalkylene polyamine, for example, the product of isostearic acid with tetraethylenepentamine. The condensation products of carboxylic acids and polyalkyleneamines may be imidazolines or amides.

The fatty acid may also be present as its metal salt, e.g., a zinc salt. These zinc salts may be acidic, neutral or basic (overbased). These salts may be prepared from the reaction of a zinc containing reagent with a carboxylic acid or salt thereof. A useful method of preparation of these salts is to react zinc oxide with a carboxylic acid. Useful carboxylic acids are those described hereinabove. Suitable carboxylic acids include those of the formula RCOOH where R is an aliphatic or alicyclic hydrocarbon radical. Among these are those wherein R is a fatty group, e.g., stearyl, oleyl, linoleyl, or palmityl. Also suitable are the zinc salts wherein zinc is present in a stoichiometric excess over the amount needed to prepare a neutral salt. Salts wherein the zinc is present from 1.1 to 1.8 times the stoichiometric amount, e.g., 1.3 to 1.6, or often about 1.33 times the stoichiometric amount of zinc, may be used. These zinc carboxylates are known in the art and are described in U.S. Pat. No. 3,367,869. Metal salts may also include calcium salts. Examples may include overbased calcium salts.

Sulfurized olefins are also well known commercial materials used as friction modifiers. A suitable sulfurized olefin is one which is prepared in accordance with the detailed teachings of U.S. Pat. Nos. 4,957,651 and 4,959,168. Described therein is a cosulfurized mixture of 2 or more reactants selected from the group consisting of at least one fatty acid ester of a polyhydric alcohol, at least one fatty acid, at least one olefin, and at least one fatty acid ester of a monohydric alcohol. The olefin component may be an aliphatic olefin, which usually will contain 4 to 40 carbon atoms. Mixtures of these olefins are commercially available. The sulfurizing agents useful in the process of the present invention include elemental sulfur, hydrogen sulfide, sulfur halide plus sodium sulfide, and a mixture of hydrogen sulfide and sulfur or sulfur dioxide.

Metal salts of alkyl salicylates include calcium and other salts of long chain (e.g. C12 to C16) alkyl-substituted salicylic acids.

Amine salts of alkylphosphoric acids include salts of oleyl and other long chain esters of phosphoric acid, with amines such as tertiary-aliphatic primary amines, sold under the tradename Primene™.

The amount of the supplemental friction modifier, if it is present, may be 0.1 to 1.5 percent by weight of the lubricating composition, such as 0.2 to 1.0 or 0.25 to 0.75 percent. In some embodiments, however, the amount of the supplemental friction modifier is present at less than 0.2 percent or less than 0.1 percent by weight, for example, 0.01 to 0.1 percent.

The compositions of the present technology can also include a detergent. Detergents as used herein are metal salts of organic acids. The organic acid portion of the detergent is a sulfonate, carboxylate, phenate, salicylate. The metal portion of the detergent is an alkali or alkaline earth metal. Suitable metals include sodium, calcium, potassium and magnesium. Typically, the detergents are overbased, meaning that there is a stoichiometric excess of metal base over that needed to form the neutral metal salt.

Suitable overbased organic salts include the sulfonate salts having a substantially oleophilic character and which are formed from organic materials. Organic sulfonates are well known materials in the lubricant and detergent arts. The sulfonate compound should contain on average 10 to 40 carbon atoms, such as 12 to 36 carbon atoms or 14 to 32 carbon atoms on average. Similarly, the phenates, salicylates, and carboxylates have a substantially oleophilic character.

While the present invention allows for the carbon atoms to be either aromatic or in paraffinic configuration, in certain embodiments alkylated aromatics are employed. While naphthalene based materials may be employed, the aromatic of choice is the benzene moiety.

Suitable compositions thus include an overbased monosulfonated alkylated benzene such as a monoalkylated benzene. Typically, alkyl benzene fractions are obtained from still bottom sources and are mono- or di-alkylated. It is believed, in the present invention, that the mono-alkylated aromatics are superior to the dialkylated aromatics in overall properties.

It is sometimes desired that a mixture of mono-alkylated aromatics (benzene) be utilized to obtain the mono-alkylated salt (benzene sulfonate) in the present invention. The mixtures wherein a substantial portion of the composition contains polymers of propylene as the source of the alkyl groups assist in the solubility of the salt. The use of mono-functional (e.g., mono-sulfonated) materials may avoid crosslinking of the molecules with less precipitation of the salt from the lubricant. It is also frequently desired to use an alkylated benzene prepared by alkylation with an α-olefin.

The salt may be "overbased." By overbasing, it is meant that a stoichiometric excess of the metal base be present over that required for the anion of the neutral salt. The excess metal from overbasing has the effect of neutralizing acids which may build up in the lubricant. Typically, the excess metal will be present over that which is required to neutralize the substrate acid at in the ratio of up to 30:1, such as 5:1 to 18:1 on an equivalent basis.

The amount of the overbased salt, that is, the detergent, utilized in the composition may be 0.025 to 3 weight percent on an oil free basis, such as 0.1 to 1.0 percent. In other embodiments, the final lubricating composition may contain no detergent or substantially no detergent or only a low amount of detergent. That is, for a calcium overbased detergent for instance, the amount may be such as to provide less than 250 parts per million calcium, e.g., 0 to 250 or 1 to 200 or 10 to 150 or 20 to 100 or 30 to 50 parts per million calcium, or less than any of the foregoing non-zero amounts. This is in contrast with more conventional formulations which may contain sufficient calcium detergent to provide 300 to 600 ppm calcium. The overbased salt is usually made up in about 50% oil and has a TBN range of 10-800 or 10-600 on an oil free basis. Borated and non-borated overbased detergents are described in U.S. Pat. Nos. 5,403,501 and 4,792,410.

The compositions of the present invention can also include at least one phosphorus acid, phosphorus acid salt, phosphorus acid ester or derivative thereof including sulfur-containing analogs in the amount of 0.002-1.0 weight percent. The phosphorus acids, salts, esters or derivatives thereof include phosphoric acid, phosphorous acid, phosphorus acid esters or salts thereof, phosphites, phosphorus-containing amides, phosphorus-containing carboxylic acids or esters, phosphorus-containing ethers, and mixtures thereof.

In one embodiment, the phosphorus acid, ester or derivative can be an organic or inorganic phosphorus acid, phosphorus acid ester, phosphorus acid salt, or derivative thereof. The phosphorus acids include the phosphoric, phosphonic, phosphinic, and thiophosphoric acids including dithiophosphoric acid as well as the monothiophosphoric, thiophosphinic and thiophosphonic acids. One group of phosphorus compounds are alkylphosphoric acid mono alkyl primary amine salts as represented by the formula

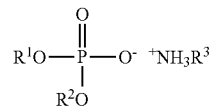

where $R^1$, $R^2$, $R^3$ are alkyl or hydrocarbyl groups or one of $R^1$ and $R^2$ can be H. The materials can be a 1:1 mixture of dialkyl and monoalkyl phosphoric acid esters. Compounds of this type are described in U.S. Pat. No. 5,354,484.

Eighty-five percent phosphoric acid is a suitable material for addition to the fully-formulated compositions and can be included at a level of 0.01-0.3 weight percent based on the weight of the composition, such as 0.03 to 0.2 or to 0.1 percent.

Other phosphorus-containing materials that may be present include dialkylphosphites (sometimes referred to as dialkyl hydrogen phosphonates) such as dibutyl phosphite. Yet other phosphorus materials include phosphorylated hydroxy-substituted triesters of phosphorothioic acids and amine salts thereof, as well as sulfur-free hydroxy-substituted di-esters of phosphoric acid, sulphur-free phosphorylated hydroxy-substituted di- or tri-esters of phosphoric acid, and amine salts thereof. These materials are further described in U.S. patent application US 2008-0182770.

Other materials can optionally be included in the compositions of the present technology, provided that they are not incompatible with the aforementioned required components or specifications. Such materials include antioxidants (that is, oxidation inhibitors), including hindered phenolic antioxidants, secondary aromatic amine antioxidants such as dinonyldiphenylamine as well as such well-known variants as monononyldiphenylamine and diphenylamines with other alkyl substituents such as mono- or di-octyl, sulfurized phenolic antioxidants, oil-soluble copper compounds, phosphorus-containing antioxidants, and organic sulfides, disulfides, and polysulfides such as 2-hydroxyalkyl, alkyl thioethers or 1-t-dodecylthio-2-propanol or sulfurized 4-carbobutoxycyclohexene or other sulfurized olefins. Also included may be corrosion inhibitors such as tolyl triazole and dimercaptothiadiazole and oil-soluble derivatives of such materials. Other optional components include seal swell compositions, such as isodecyl sulfolane or phthalate esters, which are designed to keep seals pliable. Also permissible are pour point depressants, such as alkylnaphthalenes, polymethacrylates, vinyl acetate/fumarate or /maleate copolymers, and styrene/maleate copolymers. Other materials are anti-wear agents such as zinc dialkyldithiophosphates, tridecyl adipate, and various long-chain derivatives of hydroxy carboxylic acids, such as tartrates, tartramides, tartrimides, and citrates as described in US Application 2006-0183647. These optional materials are known to those skilled in the art, are generally commercially available, and are described in greater detail in published European Patent Application 761,805. Also included can be known materials such as corrosion inhibitors (e.g., tolyltriazole, dimercaptothiadiazoles), dyes, fluidizing agents, odor masking agents, and antifoam agents. Organic borate esters and organic borate salts can also be included.

The above components can be in the form of a fully-formulated lubricant or in the form of a concentrate within a smaller amount of lubricating oil. If they are present in a concentrate, their concentrations will generally be directly proportional to their concentrations in the more dilute form in the final blend.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

substituted hydrocarbon substituents, that is, substituents containing non-hydrocarbon groups which, in the context of this invention, do not alter the predominantly hydrocarbon nature of the substituent (e.g., halo (especially chloro and fluoro), hydroxy, alkoxy, mercapto, alkylmercapto, nitro, nitroso, and sulfoxy);

hetero substituents, that is, substituents which, while having a predominantly hydrocarbon character, in the context of this invention, contain other than carbon in a ring or chain otherwise composed of carbon atoms and encompass substituents as pyridyl, furyl, thienyl and imidazolyl. Heteroatoms include sulfur, oxygen, and nitrogen. In general, no more than two, or no more than one, non-hydrocarbon substituent will be present for every ten carbon atoms in the hydrocarbyl group; typically, there will be no non-hydrocarbon substituents in the hydrocarbyl group.

It is known that some of the materials described above may interact in the final formulation, so that the components of the final formulation may be different from those that are initially added. For instance, metal ions (of, e.g., a detergent) can migrate to other acidic or anionic sites of other molecules. The products formed thereby, including the products formed upon employing the composition of the present invention in its intended use, may not be susceptible of easy description. Nevertheless, all such modifications and reaction products are included within the scope of the present invention; the present invention encompasses the composition prepared by admixing the components described above.

EXAMPLES

More detailed preparative examples of several amino esters and subsequently amino amides are provided below. It is to be understood that in each instance the desired product may not be exactly represented by the formula indicated above. For instance, there may be greater or lesser amounts of mono- or di- or tri-substituted amines present in addition to the particular formula indicated. In some instances a product or byproduct other than that of the indicated structure may even be responsible for a significant portion of the activity of the product. Thus, the structures listed herein are not intended to be limiting.

Preparative Example A (To prepare the material represented by formula (VIII) above.) Dicocoamine (a secondary amine with two predominantly C12 and C14 groups) (500 g) and toluene (1300 mL) are combined with stirring under a $N_2$ atmosphere. To this mixture chloroacetamide (120 g) is added in one portion, followed by sodium carbonate (150 g). The reaction is heated to 110° C. and stirred for 9 hours and then filtered. Approximately 12 mL of water is collected. The filtrate is dried over $MgSO_4$ and then filtered again. The filtrate is concentrated under reduced pressure using a rotary evaporator.

Preparative Example B (To prepare the material represented by formula (XII) above)

Step 1: Methanol (1000 mL) and Armeen C™ (predominantly coco-amine) (206 g) are combined in a flask with stirring. Methyl acrylate (172 g) is added over approximately 40 minutes. This is an exothermic reaction and the temperature will increase from 30 to 65° C. over the course of the addition. Once the temperature stops increasing the reactants are stirred under a nitrogen atmosphere for at least 10 hours. The reaction mixture is then concentrated under reduced pressure using a rotary evaporator.

Step 2: The product from step 1 (103 g) and xylene (750 mL) are combined with stirring and Duomeen T™ (predominantly N-tallow-propylenediamine) (176 g) is added. The reaction mixture is heated to 120° C. and stirred at this temperature for 8 hours under a nitrogen atmosphere then is heated to 140° C. for an additional 8 hours, collecting methanol in a Dean-Stark trap. At this point methanesulfonic acid is added (1.5 g) to the reaction which is re-heated to 140° C. and stirred for a further 8 hours, then cooled. The reaction is then heated to 165° C. while removing xylene. The reaction is then stirred at this temperature for a total of 12 hours then allowed to cool. The reaction mixture is concentrated under reduced pressure using a rotary evaporator.

Preparative Example C (To prepare the material represented by formula (V) above.) Armeen C™ (78 g) is added with stirring to the product of preparative example E, (see below), (130 g) in a flask under a nitrogen atmosphere. The reaction mixture is heated to 120° C. for 7 hours. The reaction mixture is then heated to approx 130° C. for an additional 7 hours, cooled, and isolated by conventional means.

Preparative Example D

Step 1: (To prepare the material represented by formula (I) above.) Armeen C™ (300 g) and methanol (200 mL) are added to a flask with stirring and methyl acrylate (134 g) is added to this mixture in one portion. This is an exothermic reaction and the temperature will increase from 30 to 60° C. over the course of the addition. Once the temperature stops increasing the combined reactants are stirred under a nitrogen atmosphere for 24 hours. The reaction mixture is then concentrated under reduced pressure using a rotary evaporator.

Step 2: (To prepare the material represented by formula (III) above.) The product from step 1 (217 g) is combined with Duomeen C™ (predominantly N-coco-propylenediamine) (204 g) with stirring under a nitrogen atmosphere. The mixture is then heated to 100° C. and stirred for 6 hours. The reaction is further heated to approx 140° C. and held there for 8 hours. The reaction mixture is then concentrated under reduced pressure using a rotary evaporator.

Preparative Example E (To prepare the material represented by formula (IV) above.) Methanol (200 mL) and Duomeen C™ (300 g) are combined in a flask with stirring under a nitrogen atmosphere. Methyl acrylate (97 g) is then added to the flask in one portion. This reaction is exothermic and the temperature increases from 30 to 58° C. during the course of the addition. The mixture is stirred under nitrogen for 24 hours. The methanol is removed by distillation.

Preparative Example F (To prepare the material represented by formula (II) above.) The product from preparative example D, step 1 (80 g) is combined with Duomeen T™ (93.5 g) in a flask with stirring under nitrogen. The reaction is then heated to approximately 120° C. and stirred at this temp for 6 hours. The reaction is allowed to cool overnight then re-heated to 150° C. and stirred at this temperature for a further 6 hours. The reaction mixture is cooled and the product isolated by conventional means.

Preparative Example G

Step 1: (To prepare the material represented by formula (VI) above.) Triameen C™ (predominantly cocodipropylenetriamine) (250 g) and methanol (150 g) are combined in a flask with stirring under a nitrogen atmosphere. Methyl acrylate (68 g) is then added drop-wise over 30 minutes. The reaction is exothermic and the temperature increases from 18 to 40° C. during the course of the addition. The reaction mixture is then stirred for 12 hours. The reaction mixture is then concentrated under reduced pressure using a rotary evaporator (80 C).

Step 2: (To prepare the material represented by formula (VII) above.) The product from step 1 (151 g) is added to Armeen C™ (75 g) with stirring under a nitrogen atmosphere. The mixture is then heated to 120° C. and held for 4 hours. The temperature is then increased to 130° C. and held for 12 hours, the reaction is then allowed to cool. The reaction mixture is then concentrated under reduced pressure using a rotary evaporator.

Preparative Example H

Step 1: (To prepare the material represented by formula (XIII) above.) Duomeen T™ (336 g) and 200 mL methanol are added to a flask with stirring and under a nitrogen atmosphere at room temperature until combined. Methyl acrylate (86 g) is added to the reaction mixture in one portion. The reaction is exothermic and increases in temperature to 54° C. during the course of the addition. The reaction is allowed to cool to room temperature and is stirred for 6 hrs. Methanol is removed under reduced pressure at 60° C.

Step 2: (To prepare the material represented by formula (XIV) above.) Oleyl amine (88 g) and the product from step 1 (139 g) are combined and heated to 120° C. with stirring and under a $N_2$ atmosphere for 5 hrs, then heated to 150° C. for and additional 8 hrs, and then the reaction is then allowed to cool. The reaction mixture is then concentrated under reduced pressure using a rotary evaporator.

Preparative Example I (To prepare the material represented by formula (XV) above)

Step 1. Oleyl amine (282 g) and 200 mL methanol are combined and stirred at room temperature. Methyl acrylate (86 g) is added in one portion. This is an exothermic reaction and the temperature will increase to 46° C. over the course of the addition. The reaction is allowed to cool to room temperature and then is stirred for 6 hours. The methanol is removed under reduced pressure.

Step 2. Duomeen™T (95 g) and the product from step 1 (100 g) are combined with stirring under a nitrogen atmosphere and heated to 120° C. for 5 hours. The mixture is then heated to 150° C. for 8 hours. The reaction mixture is cooled and the product isolated by conventional means.

Three base formulations are prepared in which representative amine materials as prepared above may be tested.

Base formulation A:
3.5% succinimide dispersant(s) (containing 41.5% oil)
0.2% dibutyl phosphite
0.1% phosphoric acid
0.1% borate ester
0.9% amine antioxidant
0.4% seal swell agent
1.1% calcium sulfonate detergents (containing 50% oil)
0.06% substituted thiadiazole
0.2% pour point depressant
0.04% ethoxylated amine
9.6% dispersant viscosity modifier (containing 25% oil)
0.04% other minor components
balance: mineral oils (predominantly 3-6 cSt)
Base formulation B:
3.5% succinimide dispersant(s) (containing 41.5% oil)
0.2% dibutyl phosphite
0.1% phosphoric acid 0.9% amine antioxidant
0.4% seal swell agent
0.2% pour point depressant
9.6% dispersant viscosity modifier (containing 25% oil)
0.03% other minor components
balance: mineral oils (predominantly 3-6 cSt)
Base formulation C:
5.0% succinimide dispersant(s) (containing 41.5% oil)
0.8% amine antioxidant
0.2% dibutyl phosphite
0.03% phosphoric acid
9.0% dispersant viscosity modifier (containing 25% oil)
0.055% other minor components
balance: mineral oils (predominantly 3-6 cSt)
(Note: the above succinimide dispersants may be borated and/or terephthalated)

Lubricants for testing are prepared by adding one of the materials from the preparative examples identified in the tables below to the indicated base formulation. The resulting lubricants are subjected to a VSFT test, which is a variable speed friction test. The VSFT apparatus consists of a disc that can be metal or another friction material which is rotated against a metal surface. The friction materials employed in the particular tests are various commercial friction materials commonly used in automatic transmission clutches, as indicated in the Tables. The test is run over three temperatures and two load levels. The coefficient of friction measured by the VSFT is plotted against the sliding speed (50 and 200 r.p.m.) over a number speed sweeps at a constant pressure. The results are initially presented as slope of the $\mu$-v curve as a function of time, reported for 40, 80, and 120° C. and 24 kg and 40 kg (235 and 392 N) force, determined at 4 hour intervals from 0 to 52 hours. Typically, the slope will initially be positive, with a certain amount of variability, and may gradually decrease, possibly becoming negative after a certain period of time. Longer duration of positive slope is desired.

The data is initially collected as a table of slope values as a function of time, for each run. For ease of analysis and comparison, each formulation at each temperature is assigned a "slope score." At each temperature, the fraction of slope values within the first 7 time measurements (0 to 24 hours) at 24 kg and of the first 7 measurements at 40 kg (thus 14 measurements total) that are positive, as a percent, is denoted as "A". The fraction of the slope values at the two pressures (14 measurements total) within the second 24 hours (28-52 hours) that are positive are denoted as "B". The slope score is defined as A+2B. The extra weighting given to the latter portion of the test is to reflect the greater importance (and difficulty) of preparing a durable fluid that retains a positive slope in the latter stages of the test. The maximum score of 300 denotes a fluid that exhibits a consistently positive slope through the entire test. For illustration, the individual slope results for Preparative Example A at 0.25% in Formulation A are presented below, along with the of the "slope score."

Preparative Example A, 0.25%, 40° C., Formulation A

| Time, hr | $\mu$-V Slope, 24 kg | $\mu$-V Slope, 40 kg | | Slope Score (A + 2B) |
|---|---|---|---|---|
| 0 | 0.009 | 0.003 | A = 11/14 | 78.6 + 2 × 14.3 = 107 |
| 4 | 0.005 | 0.006 | = 78.6% | |
| 8 | 0.006 | 0.003 | | |
| 12 | −0.001 | 0.006 | | |
| 16 | 0.005 | 0.002 | | |
| 20 | 0.001 | 0.001 | | |
| 24 | −0.001 | −0.003 | | |

-continued

| Time, hr | $\mu$-V Slope, 24 kg | $\mu$-V Slope, 40 kg | | Slope Score (A + 2B) |
|---|---|---|---|---|
| 28 | 0.002 | −0.003 | B = 2/14 | |
| 32 | −0.009 | 0.002 | = 14.3% | |
| 36 | −0.007 | −0.004 | | |
| 40 | −0.006 | −0.006 | | |
| 44 | −0.006 | −0.007 | | |
| 48 | −0.007 | −0.005 | | |
| 52 | −0.011 | −0.007 | | |

A summary of the "slope scores" for certain of the materials of the present technology is provided in the table below:

| Prep Ex. | Treat. Ex. | Treat. % | Base Formulation | Friction Mat'l[a] | Slope Score 40° C. | Slope Score 80° C. | Slope Score 120° C. |
|---|---|---|---|---|---|---|---|
| 1 | A | 0.25 | A | 7189 | 107 | 93 | 186 |
| 2 | A | 1 | A | 7189 | 179 | 250 | 300 |
| 3 | A | 2.5 | A | 7189 | 171 | 214 | 214 |
| 4 | B | 1 | A | 4211 | 143 | 186 | 229 |
| 5 | B | 2.5 | A | 4211 | 300 | 300 | 300 |
| 6 | C | 0.25 | A | 7189 | 79 | 186 | 229 |
| 7 | C | 1 | A | 7189 | 171 | 300 | 300 |
| 8 | D[b] | 0.25 | A | 7189 | 36 | 100 | 214 |
| 9 | D[b] | 1 | A | 7189 | 100 | 157 | 214 |
| 10 | E | 0.25 | A | 7189 | 50 | 100 | 186 |
| 11 | E | 1 | A | 7189 | 79 | 157 | 200 |
| 12 | F | 0.25 | A | 0512 | 86 | 271 | 300 |
| 13 | F | 1 | A | 7189 | 143 | 264 | 286 |
| 14 | G | 0.25 | A | 7189 | 93 | 157 | 157 |
| X[d] | none | 0 | A | 7189 | 19[c] | 95[c] | 159[c] |
| 15 | A | 1 | B | 7189 | 21 | 93 | 171 |
| 16 | A | 2.5 | B | 7189 | 179 | 286 | 300 |
| 17 | A | 1 | B | 4211 | 200 | 264 | 300 |
| 18 | A[e] | 2.5 + 1[e] | B | 4211 | 229 | 243 | 257 |
| 19 | B | 1 | B | 4211 | 129 | 229 | 243 |
| 20 | B | 2.5 | B | 4211 | 300 | 300 | 300 |
| 21 | C | 1 | B | 7189 | 43 | 71 | 136 |
| Y[d] | none | 0 | B | 4211 | 0 | 14 | 200 |
| Z[d] | none | 0 | B | 7189 | 0 | 0 | 64 |
| 22 | H | 0.35 | C | 0512 | 64 | 114 | 186 |
| 23 | I | 0.35 | C | 0512 | 57 | 186 | 214 |

[a]Friction materials: Raybestos ™ 7189, Raybestos ™ 4211, or Dynax ™ 0512
[b]Product of step 2 of Preparative Example D
[c]Average of 3 runs
[d]A reference example
[e]2.5% material according to preparative example A + 1% of the condensate of N-cocopropylenediamine and myristic acid The results show desirable frictional performance by materials of the present technology, in particular as compared to the base formulations from which they are absent. The results also indicate that better performance is sometimes obtained at relatively higher concentrations of 0.35 or 0.5 percent or greater, e.g., 1.0 or 2.5% compared with 0.25%. (The relatively low values for Example 15, using an otherwise very good friction modifier from preparative example A, are not completely explained and are suspected to be a result of an experimental problem. It is noted that the values are nevertheless dramatically better than those of Reference Example Z.)

Some of the materials tested exhibit exceptionally good performance. Especially noteworthy in this regard is the material of Preparative Example B, Formula (XII), which may be designated as 3,3'-(cocoazanediyl)bis(N-(3-(tallowamino)propyl)propanamide) or alternatively as N,N'-bis(tallowamino-propyl)-4-coco-4-aza-1,7-heptanediamide. It is to be understood that the coco and tallow groups in Formula (XII) and in the nomenclature may be more generally represented by hydrocarbyl or alkyl groups of 12 to 22 carbon atoms.

Each of the documents referred to above is incorporated herein by reference. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil, which may be customarily present in the commercial material, unless otherwise indicated. It is to be understood that the upper and lower amount, range, and ratio limits set forth herein may be independently combined. Similarly, the ranges and amounts for each element of the invention can be used together with ranges or amounts for any of the other elements. As used herein, the expression "consisting essentially of" permits the inclusion of substances that do not materially affect the basic and novel characteristics of the composition under consideration.

What is claimed is:

1. A method for lubricating a transmission, comprising supplying thereto a lubricant comprising:
   an oil of lubricating viscosity; and
   a hydrocarbyl amine, the hydrocarbyl group thereof having about 12 to about 22 carbon atoms, said amine having one or two groups in addition to said hydrocarbyl group, on one or more amine nitrogen atoms thereof, such additional group or groups independently being of the structure —$R^3$—C(=O)X($R^4$)$_c$, wherein each $R^3$ is independently an alkylene group containing 1 to 4 carbon atoms or a group comprising a chain of 2 to 9 carbon atoms interrupted by one or two nitrogen or oxygen atoms within the chain; X is nitrogen or oxygen; c is 2 when X is nitrogen and 1 when X is oxygen; and each $R^4$ is independently a hydrocarbyl group of 1 to about 20 carbon atoms or a group represented by the formula —$R^3$—NH$R^5$ wherein $R^5$ is a hydrocarbyl group of about 12 to about 22 carbon atoms, or, if X is nitrogen, $R^4$ may be H;
   wherein the amine comprises two groups of the structure —$R^3$—C(=O)X($R^4$)$_c$ on an amine nitrogen atom.

2. A method for lubricating a transmission, comprising supplying thereto a lubricant comprising:
   an oil of lubricating viscosity; and
   a hydrocarbyl amine, the hydrocarbyl group thereof having about 12 to about 22 carbon atoms, said amine having one or two groups in addition to said hydrocarbyl group, on one or more amine nitrogen atoms thereof, such additional group or groups independently being of the structure —$R^3$—C(=O)X($R^4$)$_c$, wherein each $R^3$ is independently an alkylene group containing 1 to 4 carbon atoms or a group comprising a chain of 2 to 9 carbon atoms interrupted by one or two nitrogen or oxygen atoms within the chain; X is nitrogen or oxygen; c is 2 when X is nitrogen and 1 when X is oxygen; and each $R^4$ is independently a hydrocarbyl group of 1 to about 20 carbon atoms or a group represented by the formula —$R^3$—NH$R^5$ wherein $R^5$ is a hydrocarbyl group of about 12 to about 22 carbon atoms, or, if X is nitrogen, $R^4$ may be H,
   wherein the amine comprises multiple amine nitrogen atoms, at least two of which bear a group of the structure —$R^3$—C(=O)X($R^4$)$_c$.

3. The method of claim 1 wherein the hydrocarbyl amine is represented by the formula:

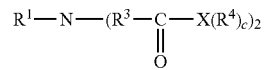

wherein $R^1$ is a hydrocarbyl group of about 12 to about 22 carbon atoms, or $R^1$ is an aminoalkyl group of up to 3 carbon atoms substituted on the nitrogen atom thereof by a hydrocarbyl group of 2 to about 22 carbon atoms.

4. The method of claim 1 wherein each $R^3$ is independently —CH$_2$CH$_2$— or —CH$_2$— or —CH$_2$CH$_2$CH$_2$NHCH$_2$— or —CH$_2$CH$_2$CH$_2$NHCH$_2$CH$_2$— or —CH$_2$—CH(CH$_3$)—.

5. The method of claim 1 wherein $R^3$ is —CH$_2$CH$_2$— or —CH$_2$— or —CH$_2$CH$_2$CH$_2$NHCH$_2$— and X is oxygen and $R^4$ is CH$_3$.

6. A method for lubricating a transmission, comprising supplying thereto a lubricant comprising:
   an oil of lubricating viscosity; and
   a hydrocarbyl amine, the hydrocarbyl group thereof having about 12 to about 22 carbon atoms, said amine having one or two groups in addition to said hydrocarbyl group, on one or more amine nitrogen atoms thereof, such additional group or groups independently being of the structure —$R^3$—C(=O)X($R^4$)$_c$, wherein each $R^3$ is independently an alkylene group containing 1 to 4 carbon atoms or a group comprising a chain of 2 to 9 carbon atoms interrupted by one or two nitrogen or oxygen atoms within the chain; X is nitrogen or oxygen; c is 2 when X is nitrogen and 1 when X is oxygen; and each $R^4$ is independently a hydrocarbyl group of 1 to about 20 carbon atoms or a group represented by the formula —$R^3$—NH$R^5$ wherein $R^5$ is a hydrocarbyl group of about 12 to about 22 carbon atoms, or, if X is nitrogen, $R^4$ may be H,
   wherein the hydrocarbyl amine comprises a material represented by the formula

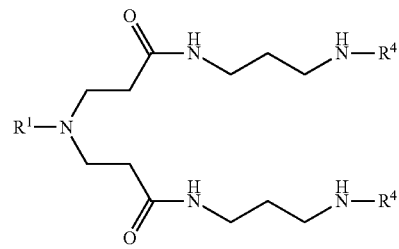

wherein $R^1$ is a hydrocarbyl group of about 12 to about 22 carbon atoms and each $R^4$ is independently a hydrocarbyl group of 1 to about 20 carbon atoms, or H, or a group represented by the formula —$R^3$—NH$R^5$ wherein $R^5$ is a hydrocarbyl group of about 12 to about 22 carbon atoms.

7. The method of claim 1 wherein the amount of the hydrocarbylamine is about 0.1 to about 10 weight percent.

8. A composition comprising:
   an oil of lubricating viscosity; and a hydrocarbyl amine, the hydrocarbyl group thereof having about 12 to about 22 carbon atoms, said amine having two groups in addition to said hydrocarbyl group, on an amine nitrogen atom thereof, such additional groups independently being of the structure —$R^3$—C(=O)X($R^4$)$_c$, wherein each $R^3$ is independently an alkylene group containing 1 to 4 carbon atoms or a group comprising a chain of 2 to 9 carbon atoms interrupted by one or two nitrogen or oxygen atoms within the chain; X is nitrogen or oxygen; c is 2 when X is nitrogen and 1 when X is oxygen; and each $R^4$ is independently a hydrocarbyl group of 1 to about 20 carbon atoms or a group represented by the formula —$R^3$—NH$R^5$ wherein $R^5$ is a hydrocarbyl group of about 12 to about 22 carbon atoms, or, if X is nitrogen, $R^4$ may be H.

9. The composition of claim 8 wherein the amine comprises multiple amine nitrogen atoms, at least two of which bear a group of the structure
—$R^3$—C(=O)X($R^4$)$_c$.

10. The composition of claim 8 wherein the hydrocarbyl amine is represented by the formula:

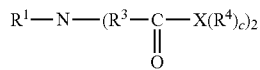

wherein $R^1$ is a hydrocarbyl group of about 12 to about 22 carbon atoms, or $R^1$ is an aminoalkyl group of up to 3 carbon atoms substituted on the nitrogen atom thereof by a hydrocarbyl group of about 12 to about 22 carbon atoms.

11. The composition of claim 10 wherein $R^1$ is an alkyl group of about 12 to about 18 carbon atoms.

12. The composition of claim 10 wherein $R^1$ is a cocoalkyl group or a tallowalkyl group or a hydrogenated talllowalkyl group.

13. The composition of claim 8 wherein each $R^3$ is independently —CH$_2$CH$_2$— or —CH$_2$— or —CH$_2$CH$_2$CH$_2$NHCH$_2$— or —CH$_2$CH$_2$CH$_2$NHCH$_2$CH$_2$— or —CH$_2$CH(CH$_3$)—.

14. The composition of claim 8 wherein X is O and $R^4$ is —CH$_3$ or —CH$_2$CH$_2$CH$_2$NH-coco, where coco is a cocoalkyl group.

15. The composition of claim 8 wherein the hydrocarbyl amine comprises a material represented by the formula

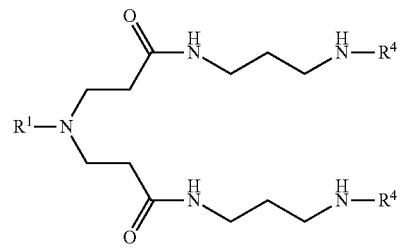

wherein $R^1$ is a hydrocarbyl group of about 12 to about 22 carbon atoms and each $R^4$ is independently a hydrocarbyl group of 1 to about 20 carbon atoms, or H, or a group represented by the formula —$R^3$—NH$R^5$ wherein $R^5$ is a hydrocarbyl group of about 12 to about 22 carbon atoms.

16. The composition of claim 8 wherein the amount of the hydrocarbylamine is about 0.1 to about 10 weight percent.

17. The composition of claim 8 wherein the lubricant further comprises at least one further additive selected from the group consisting of dispersants, detergents, antioxidants, seal swell agents, anti-wear agents, organic borate esters, organic borate salts, organic phosphorus esters, organic phosphorus salts, inorganic phosphorus acids, and inorganic phosphorus salts.

18. The method of claim 2 wherein
$R^3$ is —CH$_2$CH$_2$— or —CH$_2$— or —CH$_2$CH$_2$CH$_2$NHCH$_2$— and X is oxygen and $R^4$ is CH$_3$.

19. The method of claim 2 wherein the amount of the hydrocarbylamine is about 0.1 to about 10 weight percent.

20. The method of claim 6 wherein the amount of the hydrocarbylamine is about 0.1 to about 10 weight percent.

* * * * *